United States Patent [19]

Andrews

[11] Patent Number: 5,176,515
[45] Date of Patent: Jan. 5, 1993

[54] DENTAL TREATMENT METHOD AND APPARATUS

[76] Inventor: Lawrence F. Andrews, 6101 La Jolla Mesa Drive, La Jolla, Calif. 92037

[21] Appl. No.: 698,767

[22] Filed: May 10, 1991

[51] Int. Cl.$^5$ .................... A61D 3/00; A61C 11/00; A61C 19/04
[52] U.S. Cl. .................... 433/24; 433/54; 433/55; 433/56; 433/68; 433/73
[58] Field of Search .................. 433/54, 55, 56, 60, 433/64, 68, 73, 24; 33/512, 513, 514

[56] References Cited

U.S. PATENT DOCUMENTS

| | | | |
|---|---|---|---|
| 1,045,586 | 11/1912 | Montague | 433/54 |
| 1,674,088 | 6/1928 | Bodine | 433/73 |
| 1,753,965 | 4/1930 | Ralph | 433/56 |
| 2,138,254 | 11/1938 | Mink | 433/56 |
| 2,266,434 | 12/1941 | Morrison | 433/60 |
| 2,334,643 | 11/1943 | Moore | 433/56 |
| 2,678,495 | 5/1954 | Fine | 433/55 |
| 4,096,637 | 6/1978 | Stade | 433/73 |
| 4,171,570 | 10/1979 | Seldin | 433/73 |
| 4,279,260 | 7/1981 | Stump | 33/512 |
| 4,391,589 | 7/1983 | Monfredo et al. | 433/63 |
| 4,538,987 | 9/1985 | Weissmann | 433/34 |
| 4,547,154 | 10/1985 | Pushmann | 433/56 |
| 4,624,639 | 11/1986 | Wong | 433/56 |

OTHER PUBLICATIONS

Promotional material, "Slidematic", IM/10-88/DP, Denar Corporation (undated).
Instruction Manual, "Combi Articulator", Denar Corporation (1987).
Brochure, "The Behrend Clinometer", Teledyne Hanau (undated).
Promotional material, "To look natural and pleasing . . . ," Teledyne Hanau (undated).
Advertisement, "Disposable Articulator . . . , "Dentist, vol. 66, No. 2, Mar./Apr. 1988.
Teledyne Hanau Advertisement, "A New Dimension in Articulators . . . , " unknown periodical (undated).
Promotional material, "A New Concept in Articulators . . . , " Teledyne Hanau (undated).
Promotional material, "For the Complete Picture . . . , " 10M/7-85/LP, Denar Corporation (undated).
Promotional material, "When You Need Instruments . . . , " 10M/11-84/ADC, Denar Corporation (undated).
Promotional material, "Mark II Articulator . . . , " IM/-10-88-DP, Denar Corporation (undated).
Promotional material, "One system, Two Applications . . . , " 2M/11-88/DP, Denar Corporation (undated).
Promotional material, "Denar Dawson Kit", IM/DP-/3-87, Denar Corporation (undated).
Brochure, "Denar Corporation Price List", Denar Corporation (1988).
Brochure, "Impressions", vol. 2, Issue 1, Denar Corporation (Jan. 1988).

*Primary Examiner*—Cary E. O'Connor
*Attorney, Agent, or Firm*—Townsend and Townsend

[57] ABSTRACT

A characteristic of optimal facial harmony is a correlation of the A/P (Anterior/Posterior) position of the maxillary incisors with the forehead. When the forehead is canted about 7 degrees or less, the A/P position of the maxillary incisors should match that of the middle of the forehead. For every degree the forehead is canted more than 7 degrees, the A/P position of the maxillary incisors should be 0.6 millimeters more anterior than the middle of the forehead. The extent to which the A/P position of the maxillary incisors is forward or back of the forehead's midpoint can be judged in millimeters quite accurately by viewing a patient in profile with the patient's forehead and maxillary incisors fully bared. Once the linear decision is made then the A/P treatment goal position can be physically measured and recorded using a novel bite fork (58), an improved facebow (56), and a new piece of equipment called a verticalizer (60). This information can then be transferred to and displayed on the occlusofacial simulator, a new kind of articulator.

55 Claims, 11 Drawing Sheets

DENTAL TREATMENT METHOD AND APPARATUS

BACKGROUND OF THE INVENTION

The teeth and jaws are the substructure for the lower two-thirds of the face. Orthodontists, oral surgeons and plastic surgeons often change the position of the teeth and jaws and, as a result, the soft tissues of the lower two-thirds of the face. Currently these specialists are using dental casts mounted on conventional articulators to show: the distance the maxillary (upper) teeth are from the temporomandibular joints (TMJs), the superior/inferior (above/below) position of the teeth relative to a third reference point, and how the teeth relate to each other. The third reference point is typically an internal reference point on the skull, such as the inferior border of the orbit (the bottom of the eye socket). In that conventional articulators do not simulate any portion of the patient's face or how the teeth relate to the face, photographs from the front and sides of the face as well as lateral radiographs of the head are used to show the relationship of the teeth to the face, to learn the extent that teeth and jaws can contribute to or detract from the harmony of the face, and to plan changes needed for full facial harmony.

Conventional dental articulators consist essentially of a one part upper member and a one part lower member coupled together by a joint which simulates the TMJs. The upper member of the articulator simulates a transverse section of the cranial base to which maxillary (upper jaw) casts can be mounted using plaster and a mounting plate. The lower member of the articulator simulates the mandible (lower jaw) to which mandibular casts can be mounted, also using plaster and a mounting plate. The mounting plates are commonly secured to the upper and lower members of the articulator using screws. Auxiliary devices, such as facebows with waxed bite forks, are used to record the anterior/posterior (A/P) distance the maxillary arch is from the TMJs, and the superior/inferior S/I position of the maxillary arch relative to a third reference point on the skull such as the inferior border of the orbit. The thin wafer of wax is used to record the orientation of the mandibular arch to the maxillary arch. These same auxiliary devices and materials are used to orient dental casts to the articulator. The casts are then secured to the articulator using mounting plates and plaster. This permits the dental casts to be oriented to the articulator's TMJs, to a third reference point, and to each other just as the teeth are oriented to these anatomical structures and to each other on a patient. However, there is no way to know with conventional articulators alone how the teeth relate to the face or to their A/P treatment goal position.

SUMMARY OF THE INVENTION

The present invention is based upon the premise that the forehead is the part of the face least likely to be abnormal and is the best site from which to judge harmony of the middle and lower face. A subsidiary basis for the present invention is that facial harmony is partially dependent upon a correlation between the A/P (anterior/posterior) position and cant (that is, the angular orientation) of the forehead and the A/P position of the maxillary incisor teeth. The A/P position of the middle of the forehead is used as the primary reference for determining the A/P treatment goal position for the maxillary incisor teeth; that A/P position is modified if the cant of the patient's forehead exceeds 7°.

Broadly, invention is directed to a method for determining, judging, measuring, recording, transferring, and displaying the orientation of the teeth to: the TMJS, the planes of the patient's head, each other, as well as to their A/P treatment goal position. The first step in finding the goal position for a patient is preferably done by having the patient pull his or her hair back from the forehead and smiling broadly enough to fully bare the maxillary crowns while keeping the head upright or vertical. The patient is then viewed in profile and a judgment is made as to the A/P position of the midpoint of the most prominent maxillary incisor crown relative to the A/P position of the center of the forehead. This judgment is made in millimeters from a hypothetical line descending from the center of the forehead while, at the same time, being parallel to the estimated midfrontal plane of the head. That is, the physician or dentist will make an estimate of the A/P distance, such as 3 mm anterior the midpoint of the most prominent maxillary incisor crown is to the hypothetical vertical line.

The inclination or cant of the patient's forehead is then measured relative to the hypothetical line (how this is done is explained later). If the cant is less than about 7°, the A/P treatment goal position for the maxillary central incisors is taken to be the same as the A/P position of the hypothetical vertical line descending from the center of the forehead. If the cant is greater than 7°, the A/P treatment goal position is taken to be the A/P position of the hypothetical line plus about 0.6 mm anterior for each degree of cant greater than 7°. An auxiliary device (the verticalizer) automatically measures the forehead's cant relative to the hypothetical line and indicates, with its free falling chain the A/P goal for the dentition's anterior limit. The actual A/P linear distance between the chain and the TMJ axis can be learned from where the chain falls, next to a scale on the facebow.

This linear information is recorded on the patient's treatment card and later is transferred to the notch on the upper anterior part of the occlusofacial simulator type of articulator that matches that linear number. A pointer is then inserted in the notch. The pointer descends and displays the newly found goal for the dentitions anterior limit. This pointer indirectly simulates a point on the forehead (between the trichion and glabella), so that the dentists and physicians involved in moving a patient's teeth and jaws can use the occlusofacial simulator to not only orient the teeth to the TMJs, each other, and the estimated planes of the head, but also to their A/P treatment goal position. The recording of information preferably is accomplished by first using a novel waxed bite fork, an improved facebow, a wax wafer, and a new piece of equipment called a verticalizer.

Conventional articulators do not permit the user to orient the teeth to the face. One of the primary advantages of the invention is that it does permit the user to orient the teeth to the face, rather than to rely solely on photographs or internal radiograph references used for that purpose. By simulating a part of the forehead, dentists and physicians involved in moving teeth and jaws can, for the first time, not only orient teeth to the TMJs and to each other, but also to the estimated planes of the head and to a point on the most stable portion of the face. The occlusofacial simulator will do what conventional articulators will do and, in addition, will show the A/P position of the most facially prominent maxillary incisor relative to its treatment goal position. This approach reduces or eliminates the way conventional facial photographs and lateral radiographs are used for diagnosing and planning the treatment goal for the dentition's anterior limit because that information can be learned directly from the face, recorded with auxiliary devices, transferred and displayed directly on the occlusofacial simulator.

Other features and advantages of the invention will appear from the following description in which the preferred embodiment has been set forth in detail in conjunction with the accompanying drawings.

BRIEF DESCRIPTION OF THE DRAWINGS

FIG. 10 shows the facebow and bite fork of FIG. 3 mounted to a patient shown in profile with the ear plugs 86 of FIG. 6 engaged in the ear holes of the patient, the waxed arch-shaped plate of the bite fork is engaged between the upper and lower teeth of the user as in FIG. 9 with the bite fork extension engaging the midpoint of the crowns of the maxillary incisor teeth of the patient; FIG. 10 also illustrates arm 108 is used to measure the angle between a line connecting the estimated TMJ axis 104 and nasion, and the body of the facebow when it parallels the estimated transverse plane of the head;

FIG. 13 illustrates the upper part of the simulator of FIG. 12 properly positioned in a horizontal attitude through the engagement of the upper and lower parts at the simulated TMJs at the posterior end and through the vertical support provided by a spacer wire supporting the anterior end of the upper part. FIG. 13 also illustrates the maxillary cast being properly mounted to the upper part of the simulator once the wet plaster hardens.

DESCRIPTION OF THE PREFERRED EMBODIMENT

Figure 1:
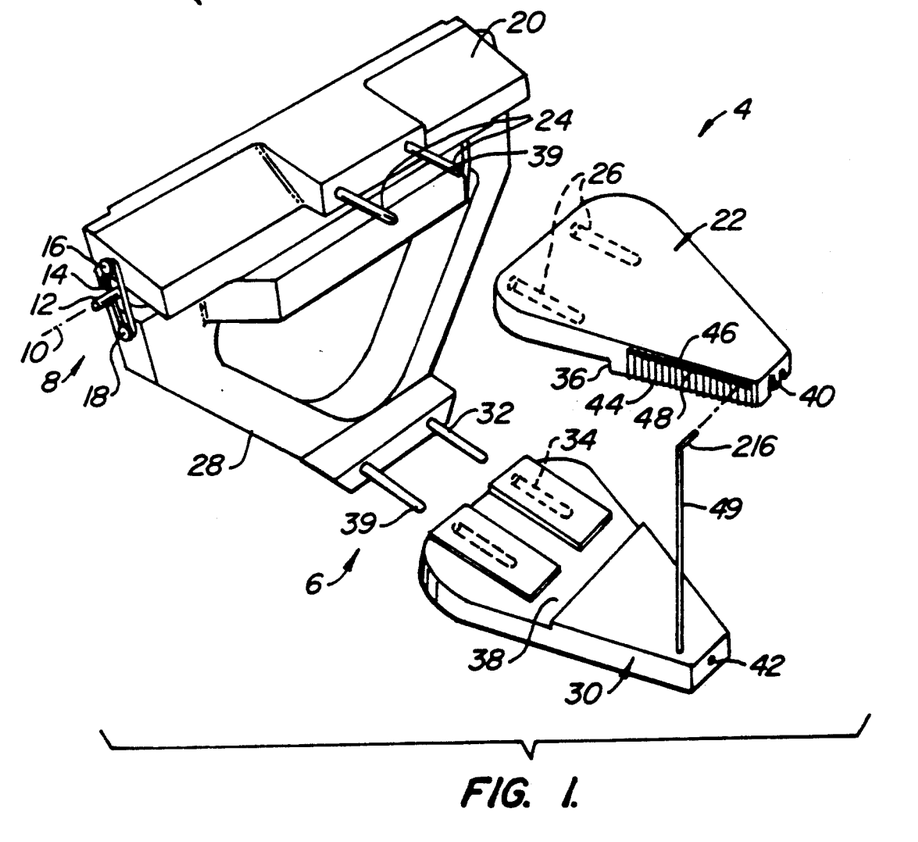
FIG. 1 is a partially exploded perspective view of an occlusofacial simulator made according to the invention.

FIG. 1 illustrates an occlusofacial simulator 2, which is a type of dental articulator. Simulator 2 includes an upper part 4 and a lower part 6 coupled at the simulated temporomandibular joints (TMJs) 8, so that upper and lower parts 4, 6 can pivot about an estimated TMJ axis 10. The simulated TMJs 8 includes extensions 12 positioned coaxially with axis 10. Extensions 12 are used to properly position a face bow described below. Upper and lower parts 4, 6 are kept together at simulated TMJs 8 by rubber bands 14 stretched between mushroom-shaped extensions 16, 18 extending from upper and lower parts 4, 6 above and below axis 10.

Figure 1A:
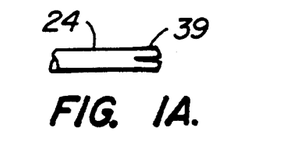
FIG. 1A is an enlarged side view of the tip of a post extending from the upper posterior part of the simulator of FIG. 1.

Upper part 4 includes a superior posterior part 20 and a superior anterior part 22 connected to one another by parallel posts 24 which extend from part 20 to engage corresponding holes 2 formed in part 22. Lower part 6 includes a generally vertically extending posterior part 28 removably coupled to a lower anterior part 30 by parallel posts 32 and holes 34. (Parts 22, 30 are also called upper and lower mounting plates 22, 30 because they are used to mount the dental casts to the articulator.) The tips 39 of posts 24, 32 are preferably slit, slightly separated and rounded on the outside to help ensure good frictional engagement of posts 24, 32, see FIG. 1A, within holes 26, 34. The use of posts and holes eliminates the need to use any screws to mount parts 22, 30 to parts 20, 28. Parts 22, 30 have undercuts 36, 38 to engage plaster which in turn holds the casts of the teeth to simulator 2. Making upper and lower parts 4, 6 as two-piece elements facilitates attaching and detaching of the plaster casts to and from the articulator when needed.

Figure 2:
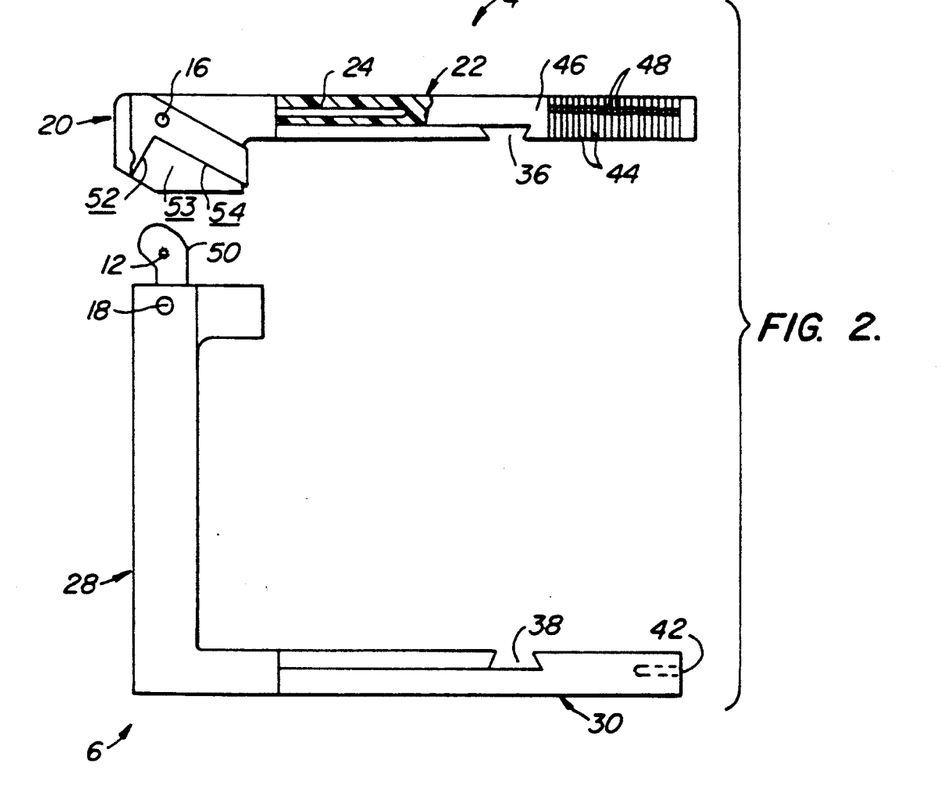
FIG. 2 is a side elevational view of the simulator of FIG. 1 with the upper and lower parts separated.
Figure 13:
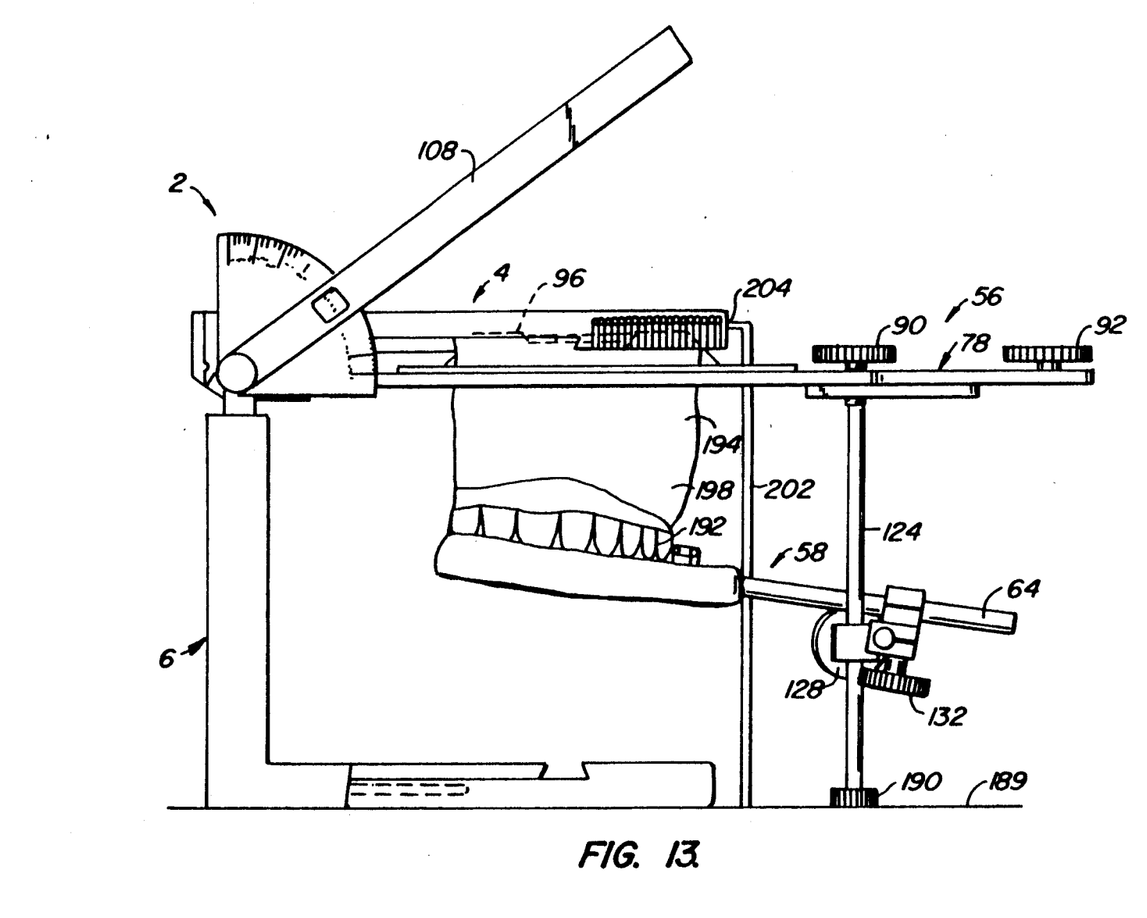

As with conventional articulators, upper part 4 simulates a transverse section of the cranial base of a patient while lower part 6 simulates the horizontal portion of the lower jaw of the patient. Parts 22, 30 have holes 40, 42 at their anterior ends used to hold wires which properly position the parts during cast mounting, as described below with reference to FIGS. 13 and 14. Part 22 also includes a series of closely spaced, vertically oriented grooves 44 formed along edge 46 of part 22. Each groove 44 has a mounting hole 48 formed near the upper end of the groove to support a vertically oriented pointer 49 for uses to be discussed below. As best shown in FIG. 2, part 28 includes extensions 50, which simulate the mandible's condyles, which engage angled surfaces 52, 53, 54 of part 20 to simulate the walls of the socket of the joint. Together parts 50, 52, 53, 54 simulate the patient's temporomandibular joint.

Figure 3:
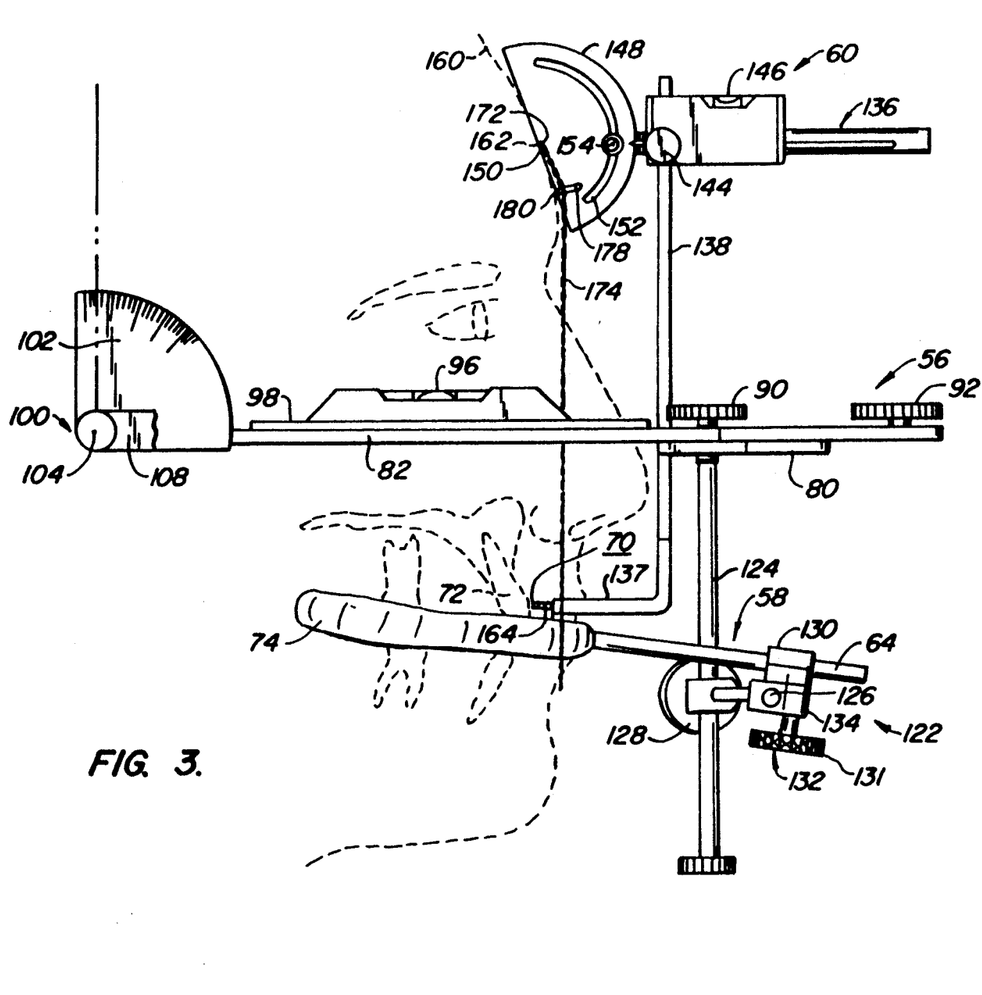
FIG. 3 is a side view of auxiliary devices used With the simulator of FIG. 1, including a facebow, bite fork and verticalizer, shown taking measurements of a patient's head.

FIG. 3 illustrates a group of accessories used with simulator 2. Broadly, the accessories include a facebow 56 connected to a bite fork 58 and a verticalizer 60 coupled to bite fork 58. These accessories will now be described individually.

Figures 4, 4A:
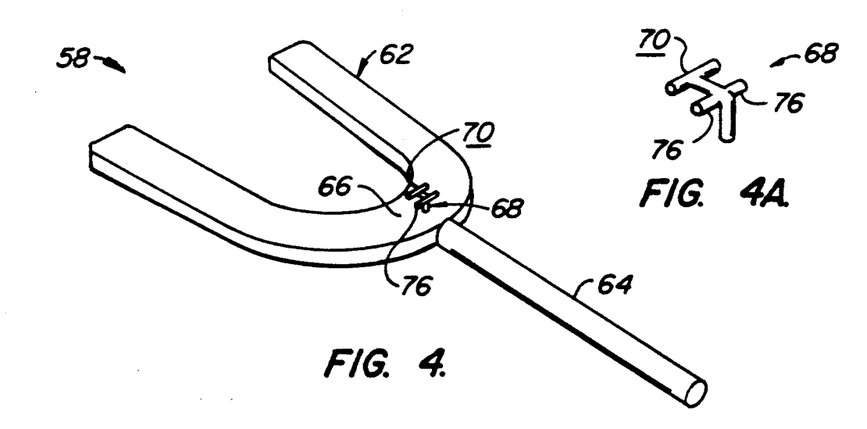
FIG. 4 is a perspective view of the bite fork of FIG. 3.
FIG. 4A is an enlarged view of the periscope-shaped extension of FIG. 4.
Figure 5:
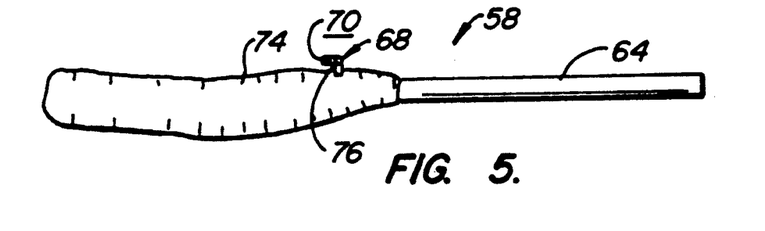
FIG. 5 is a side elevational view of the bite fork of FIG. 4 with wax mounted to the arched plate.

In FIGS. 4, 4A and 5, bite fork 58 is shown to include an arch-shaped plate 62 to which a handle 64 is mounted at the bight 66 of the arch-shaped plate 62. Bight 66 also includes a periscope-shaped extension 68, having an elongated contact surface 70 at its distal end, used to properly position bite fork 58 within the user's mouth by positioning surface 70 against the middle of the crown of the most prominent maxillary central incisor tooth 72, as shown in FIG. 3. The periscoped extension 68 also has lateral extensions 76 to which verticalizer 60 is coupled as shown in FIG. 3. Also, as shown in FIGS. 3 and 5, the arch-shaped plate 62 has a covering of wax 74 applied to its upper and lower surfaces to enable the user to take imprints of the teeth.

Figure 6:
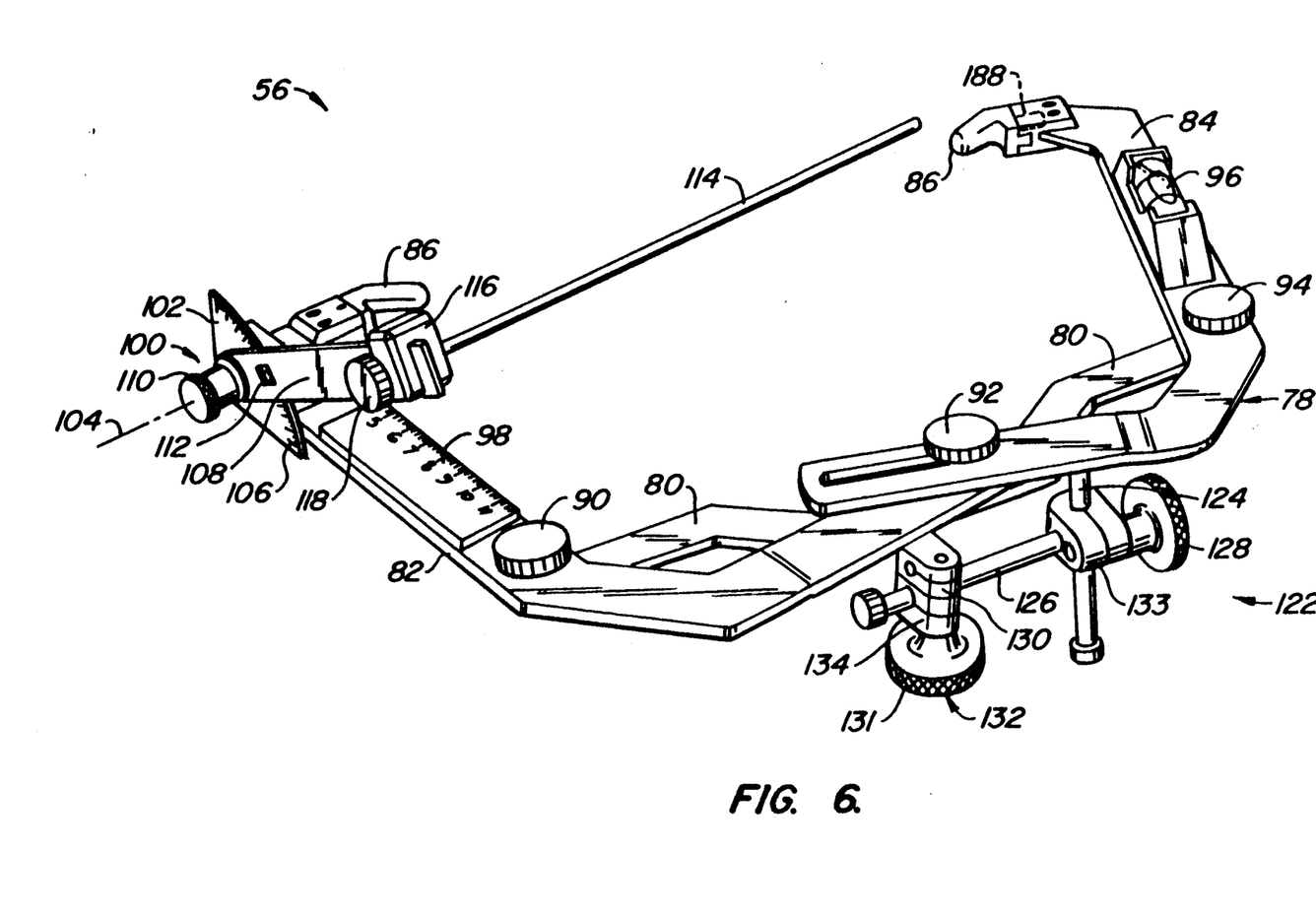
FIG. 6 is a perspective view of the facebow of FIG. 3.

Turning now to FIGS. 3 and 6, facebow 56 includes an articulated, generally U-shaped frame 78 having a base 80 and first and second legs 82, 84 with removable earplugs 86 at the posterior ends of legs 82, 84. Frame 78 is hinged together so as to permit earplugs 86 to be inserted into the patient's ear holes and then locked into place using lock nuts 90, 92, 94.

Frame 78 includes a bubble level 96 mounted to leg 84. Frame 78 is constructed so that level 96 provides an accurate indication of when frame 78, and thus a scale 98 mounted to leg 82, is horizontal. Scale 98 is used to indirectly measure the A/P distance the forehead and the maxillary incisors are from the estimated TMJ axis 104 of facebow 56.

The facebow's TMJ axis 104 is positioned approximately 10 mm anterior of the facebow's earplugs 86 just as the patient's TMJ axis is approximately 10 mm anterior of the patient's ear openings. A protractor/arm assembly 100 is mounted to leg 82. Assembly 100 includes a protractor 102 mounted to leg 82 with its axis coinciding with the facebow's TMJ axis 104. Protractor 102 is arranged with its zero angle marking 106 in a plane passing through axis 104 and parallel to frame 78. Assembly 100 also includes a pivot arm 108 secured to protractor 102 by a lock nut 110 to pivot around axis 104. Arm 108 has a readout window 112 to permit the user to determine the angle between arm 108 and frame 78. A transversely extending rod 114 is mounted along arm 108 by a sliding latch 116 which permits rod 114 to slide and then be secured along the length of arm 108 by tightening and loosening a lock nut 118 carried by latch 116. Latch 116 is configured so that rod 114 extends parallel to axis 104. As suggested in FIG. 3, when the head is upright the facebow frame parallels the estimated transverse plane of the head which, in the example, passes through the axis of the patient's TMJs.

Facebow 56 includes a facebow mounting assembly 122 having a rod 124 rigidly fixed to and vertically descending from base 80 of frame 78. Rod 24 has a base 190 at its lower end. Assembly 122 also includes a generally horizontal rod 126 secured to rod 124 by a sliding lock nut 128. One portion 134 of a piggyback swivel 132 is slidably mounted along rod 126, the other portion 130 (Which can pivot about a vertical axis in FIG. 6) is used to engage handle 64 of bite fork 58, as shown in FIG. 3, thus securing bite fork 58 to facebow 56 with lock nut 131.

Figure 7:
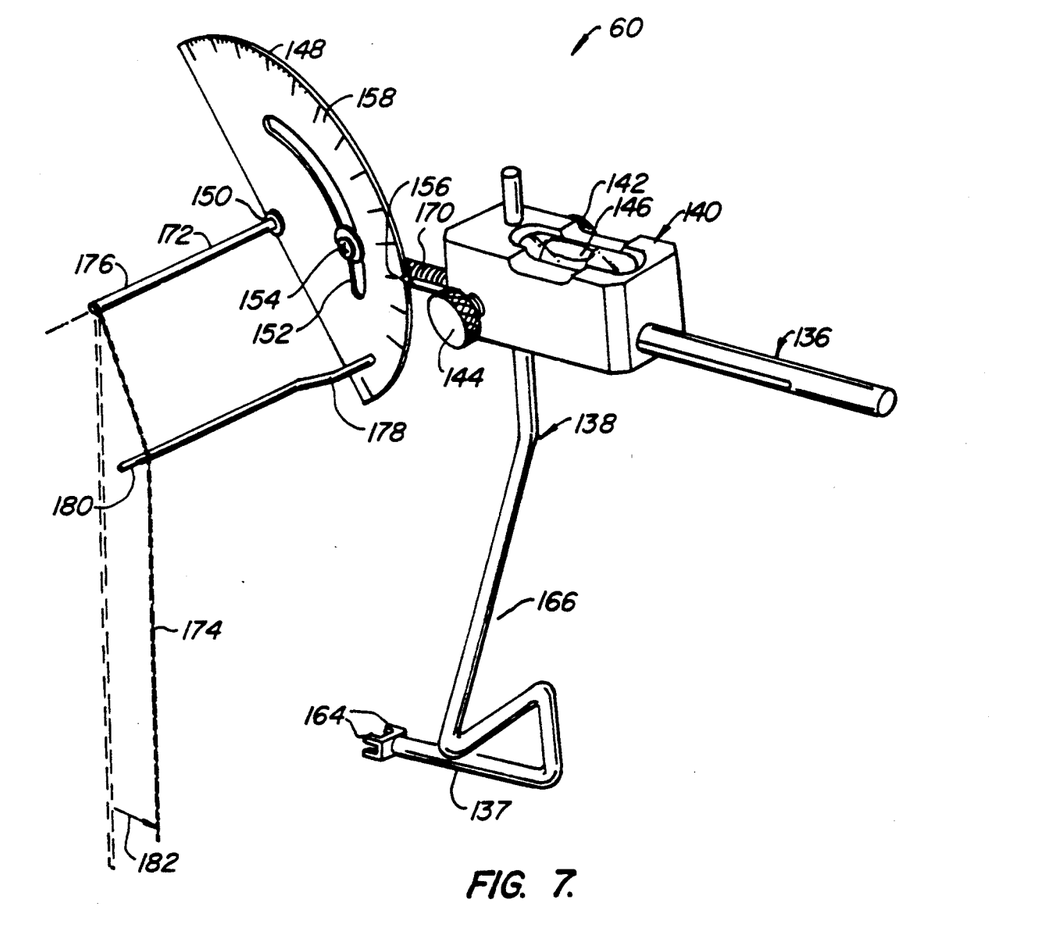
FIG. 7 is a perspective view of the verticalizer of FIG. 3.

A third auxiliary device, verticalizer 60, is shown in FIGS. 3 and 7. Verticalizer 60 includes two main, typically horizontal, rods 136 and 137 and a main, generally vertical, rod 138. Rod 136 is secured at a right angle to rod 138 by a mounting block 140. Mounting block 140 includes a pair of thumb screws 142, 44 used to secure rods 136, 138 to mounting block 140 at various positions along their lengths. Block 140 includes a level 146 which indicates when main vertical rod 138 is vertical. A fixed length positioning rod 137 is welded at a right angle to rod 138 and parallel to rod 136. Rod 137 has a pair of positioning forks 164 at its outer end sized to engage lateral extensions 76 for the reasons discussed below.

A protractor 148 is pivotally mounted to the outer end of rod 136 at pivot 150. Protractor 148 includes a slot 152 through which a lock screw 154 passes. The user locks protractor 148 in position relative to rod 136 by tightening lock screw 154. The angle of inclination of protractor 148 is indicated by a pointer 156 carried by rod 136 which points out the appropriate angular markings 158 on protractor 148. As shown in FIG. 3, protractor 148 is placed against the user's forehead, preferably so the center or mid-point 162 of the forehead is generally coincident with pivot 150; protractor 148 measures the inclination or cant of the patient's forehead relative to the vertical when the patient's head is held at a vertical attitude and rod 138 is vertical, as indicated by level 146. This angular information is used in determining the A/P goal position for the patient's maxillary incisor teeth 72.

When forks 164 of rod 137 are coupled to lateral extensions 76 of periscopic extension 68, this serves to stabilize the lower end of verticalizer 60 and to hold the lower end a specified distance from maxillary incisor 72. Rod 138 has a generally V-shaped center section to create a nose gap 166 so that the patient's nose does not interfere with the proper positioning of rod 138. Rod 136 also includes a 20 mm scale 170 (+ and −10 mm from zero) formed along its length to provide an accurate measure of the distance between pivot 150 and rod 138. The distance between pivot 150 and zero on scale 170 equals the length of rod 137. Therefore, if pivot 150 is at the center 162 of the patient's forehead 160 and pointer 156 indicates zero on scale 170 (with forks 164 engaging extensions 76 and rod 138 vertical), the A/P position of the center of the forehead matches that of the A/P position of the maxillary incisor 72.

Verticalizer 60 also includes a horizontal rod 172 extending laterally from pivot 150. A chain 174 is mounted to the outer end 176 of rod 172. Unless engaged by rod 180, chain 174 drops straight down from center 162 of forehead 160. The A/P position of center 162 of forehead 160 relative to estimated TMJ axis 104 can be learned by looking where the chain falls relative to scale 98 on facebow 56.

Verticalizer 60 includes a second horizontal rod 178 that extends laterally. Rod 178 has a doglegged or offset end 180. End 180 is configured and positioned so that chain 174 hangs straight and undisturbed so long as the cant of the patient's forehead is less than about 7°. At a cant of about 7°, end 180 contacts chain 174; for angles of cant greater than 7°, chain 174 becomes displaced in an anterior direction, that is in the direction of arrow 182. The radial distance from end 180 to horizontal support 172 is chosen so that for each angle of cant greater than 7°, chain 174 is shifted in the anterior direction approximately 0.6 mm. For cants 7° or less, rod 178 does not touch chain 174. In FIG. 7, the angle of cant is about 19° so that the anterior shift of chain 174 computes to (19°−7°) ×0.6 mm/°=12°×0.6 mm/°=7.2 mm.

The use of simulator 2 and its auxiliary devices begins with several precepts. First, teeth are part of the face, and that facial harmony characteristics include a correlation between the A/P position and cant of forehead 160 and the A/P position of maxillary incisor teeth 72, particularly in profile. Second, the A/P position of teeth 72 relative to the A/P position and cant of the forehead that most individuals would choose for themselves, given a choice, is definable. Third, the optimal A/P goal position of teeth 72 that most individuals would elect for themselves, given the choice, can be determined generally within 4 mm for a given patent with the use of external landmarks from the upper third of the face (the forehead). This provides a much more reliable basis than achieved with the goals found by using conventional diagnostic methods which use internal cephalometric landmarks or by using maxillary six year molars. Such goals can vary by as much as 13 mm for a given patient.

Prior to using any of the equipment and devices described thus far, the patient is asked to pull his or her hair back from the forehead and smile broadly while keeping the head upright or vertical. The patient is then viewed in profile and the A/P position of the maxillary central incisor is judged to the relative A/P position of the center of the forehead. That is, the dentist or physician will make an estimate of the A/P distance, such as the maxillary incisor teeth are 3 mm anterior of the center of the forehead. This number is then recorded on the patient's chart to be used later.

Figure 9:
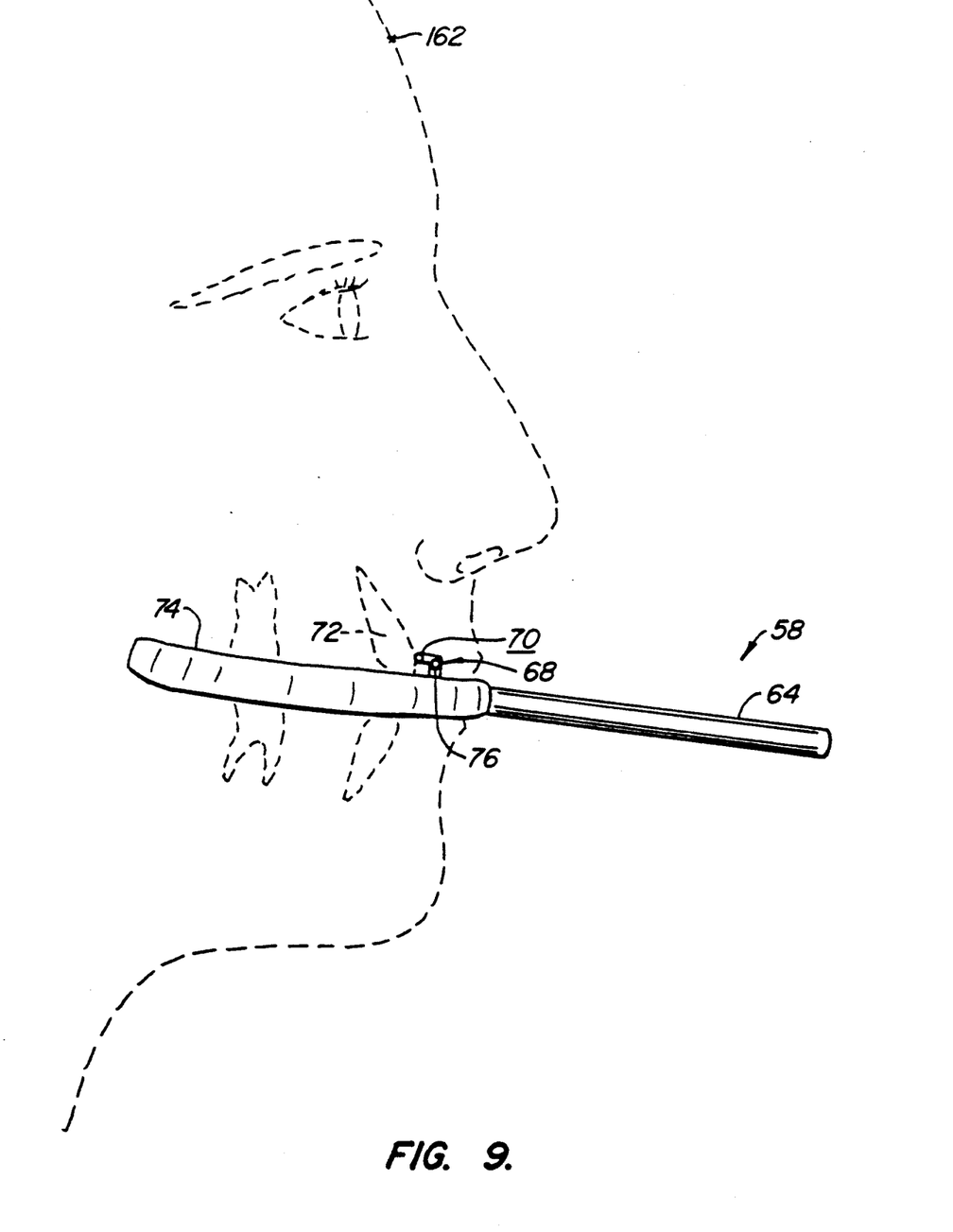
FIG. 9 shows the bite fork of FIG. 5 in use with the profile of the patient's head shown in dashed lines.

Wax 74 is then added to both sides of the arch-shaped plate 62, softened with warm water, and, while the user holds handle 64, the waxed plate is inserted into the mouth of the patient until surface 70 contacts tooth 72, as shown in FIG. 9. Arch-shaped plate 62 is then pressed superiorally (upwardly) into the maxillary (upper) teeth with sufficient force to leave imprints in wax 74 while ensuring that surface 70 of extension 68 is touching the midpoint of the face of the most prominent maxillary central incisor tooth 72. Bite fork 58 is then removed and wax 74 is cooled. Wax 74 on the inferior (lower) surface of arch-shaped plate 62 is then warmed independently of the wax on the superior portion, and the bite fork is reinserted on the maxillary arch. The patient is instructed to bite into the warm wax with sufficient force to leave indentations. Bite fork 58 is again removed to allow the wax to cool. After cooling, bite fork 58 is again inserted into the mouth of the patient, who again bites into the arched plate into the pre-formed indentations with sufficient force to hold the bite fork 58 in place. Bite fork 58 is now ready to receive facebow 56.

Earplugs 86 of facebow 56 are inserted into the patient's ear openings and frame 78 is secured into position using lock nuts 90, 92, 94. Lock nuts 128 and 131 are loosened and handle 64 of bite fork 58 and portion 130 of piggyback swivel 132 are engaged. Facebow 56 is adjusted up or down until level 96 indicates that frame 78 is horizontal, while the patient maintains his or her head in a vertical attitude. When this occurs, swivels 130, 133, 134 are tightened with locknuts 128, 131 to secure bite fork 58 to facebow 56.

Referring now to FIGS. 3 and 7, verticalizer 60 is now adjusted to the patient in two ways. First, thumb screw 142 is loosened until the distance between rods 136 and 137 equals the distance between the middle 162 of the forehead 160 and the middle of the face of the crown of the most prominent maxillary central incisor 72. Second, thumb screw 144 is loosened and rod 136 is adjusted in or out until the scale 170 inversely matches the distance the midpoint of the maxillary incisor was previously judged to be forward or back of the midpoint of the forehead (e.g., 3 mm anterior). It is then recorded on the patient's chart to be used later. Then pivot 150 is located at center 162 of forehead 160, and forks 164 are engaged with lateral extensions 76 of periscope extension 68 of bite fork 58. The patient then moves his or her head up or down until level 146 indicates rod 138 is vertical. Now the locknuts of mounting assembly 122 that connect bitefork 58 to facebow 56 are loosened and, while the verticalizer's level 146 still reads zero, the front of the facebow is adjusted up or down until its level 96 also reads zero. When this is accomplished the distance between the midpoint of the crown of the most prominent maxillary incisor tooth 72 and the estimated TMJ axis 104 is thus recorded by these two auxiliary devices. See FIG. 10.

It should be noted that it is the dentist's or physician's initial, visual assessment of the A/P position of the most prominent maxillary incisor tooth 72 relative to the A/P position of the center 162 of the forehead 160 which determines the orientation of everything else which follows. That is, once locknuts 142, 144 are tightened and the verticalizer is in position, the user tilts patient's head until level 146 indicates a level orientation. (This is in contrast to moving the patient's head until it is level (by whatever criterion is used) and then adjusting verticalizer 60 until level 146 indicates rod 136 is horizontal.) It has been found that with some practice, dentists and physicians can make this estimate quite accurately, especially since what is important is visual perception rather than absolute accuracy.

Positioning protractor 148 against forehead 160 automatically orients the protractor to the cant of the patient's forehead. At the same time, depending upon the cant of the forehead, the chain-engaging, dogleg-shaped end 180 at the end of rod 178 engages chain 174 and moves the chain about 0.6 mm in the anterior direction for every degree the cant exceeds 7°. The user can read the position scale 98 of facebow 56, which gives a direct reading of the A/P goal position for the maxillary central incisor tooth 72 relative to estimated TMJ axis 104. This measurement is recorded on the patient's record chart and indicates which hole 48 (see FIG. 1) pointer 49 is to be inserted in. The verticalizer 60 is now removed from the patient.

Figure 10:
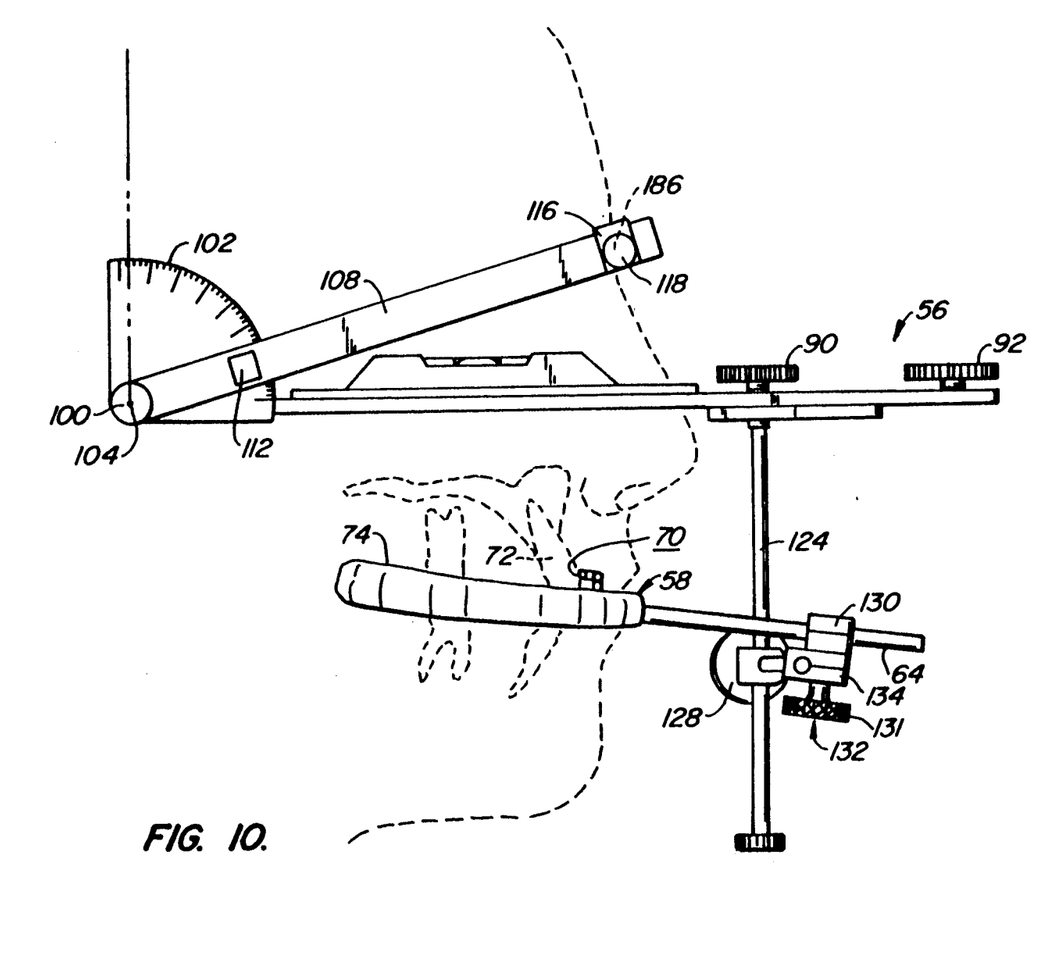

The angle between the facebow frame 78 (which represents the estimated transverse plane of the head) whose plane passes through estimated TMJ axis 104, and a line connecting TMJ axis 104 and the nasion 186 (the depression between the top of the nose and the base of the forehead, shown in FIGS. 3, 10) is measured by adjusting rods 108 and 114 to the nasion. This angle is read at window 112 and recorded on the patient's written chart, and is used to relocate the facebow to the estimated transverse plane of the head when subsequent mountings are done. This approach permits relocating the facebow to the transverse plane of the patient's head without having to again judge the A/P incisor position and to use verticalizer 60 every time progress dental casts of the patient are needed. Facebow 56 and bite fork 58 are then removed as a unit from the patient in preparation for transfer to simulator 2.

Figure 8:
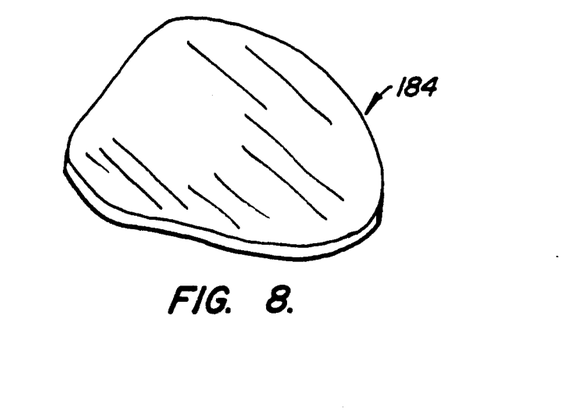
FIG. 8 is a perspective view of a wax wafer.
Figure 11:
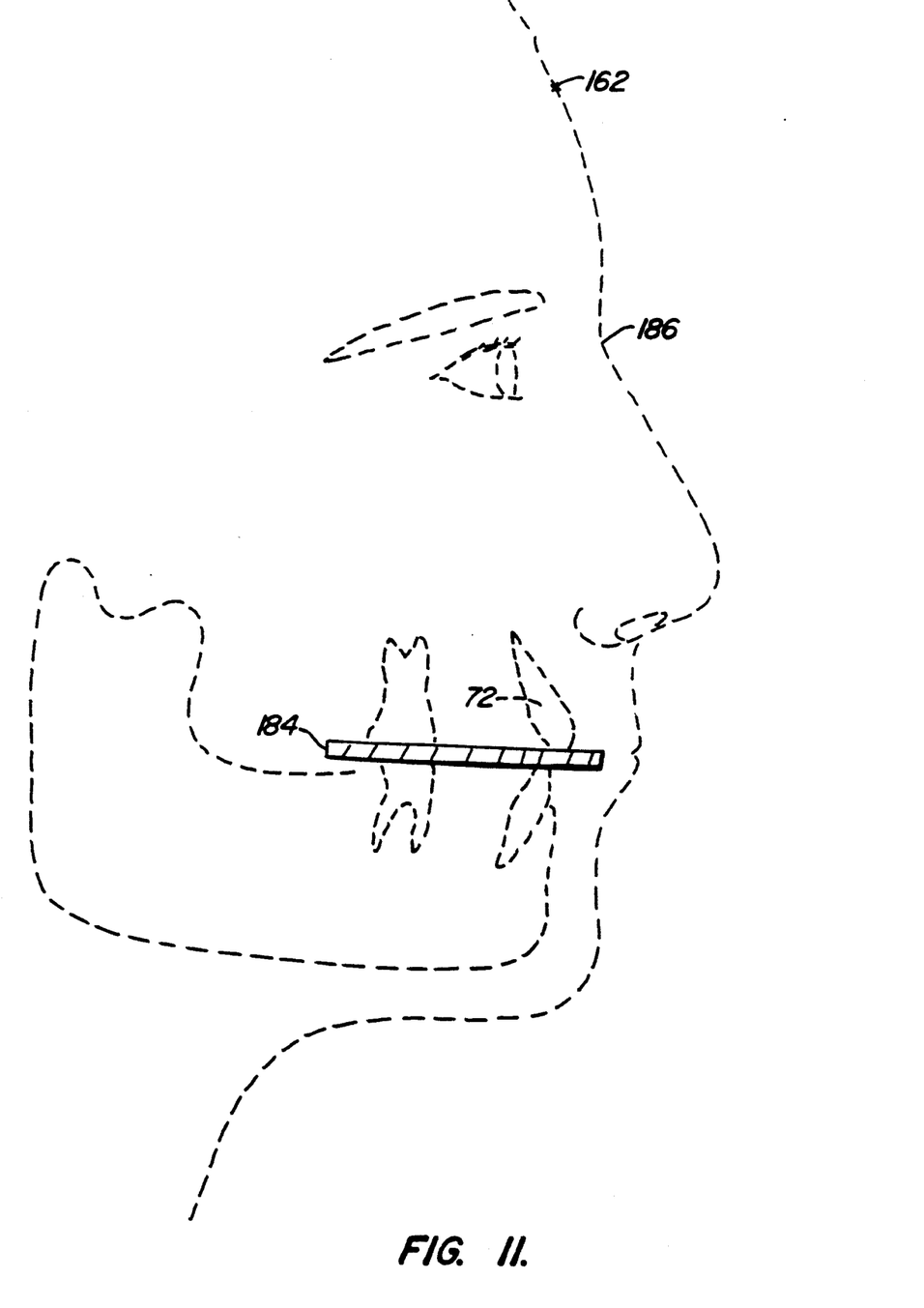
FIG. 11 illustrates the wax wafer of FIG. 8 being used to record the orientation of the mandibular teeth to the maxillary teeth.

A wax wafer 184 (FIG. 8) is used to record the relationship of the maxillary teeth to the mandibular teeth by having the patient bite into the wax wafer when closing in centric relation (FIG. 11). This leaves indents in the wax wafer providing a bite registration. The bite registration is later used to orient a mandibular cast 208 to a maxillary cast 192 after the maxillary cast has been mounted on simulator 2 (FIG. 14).

Figure 12:
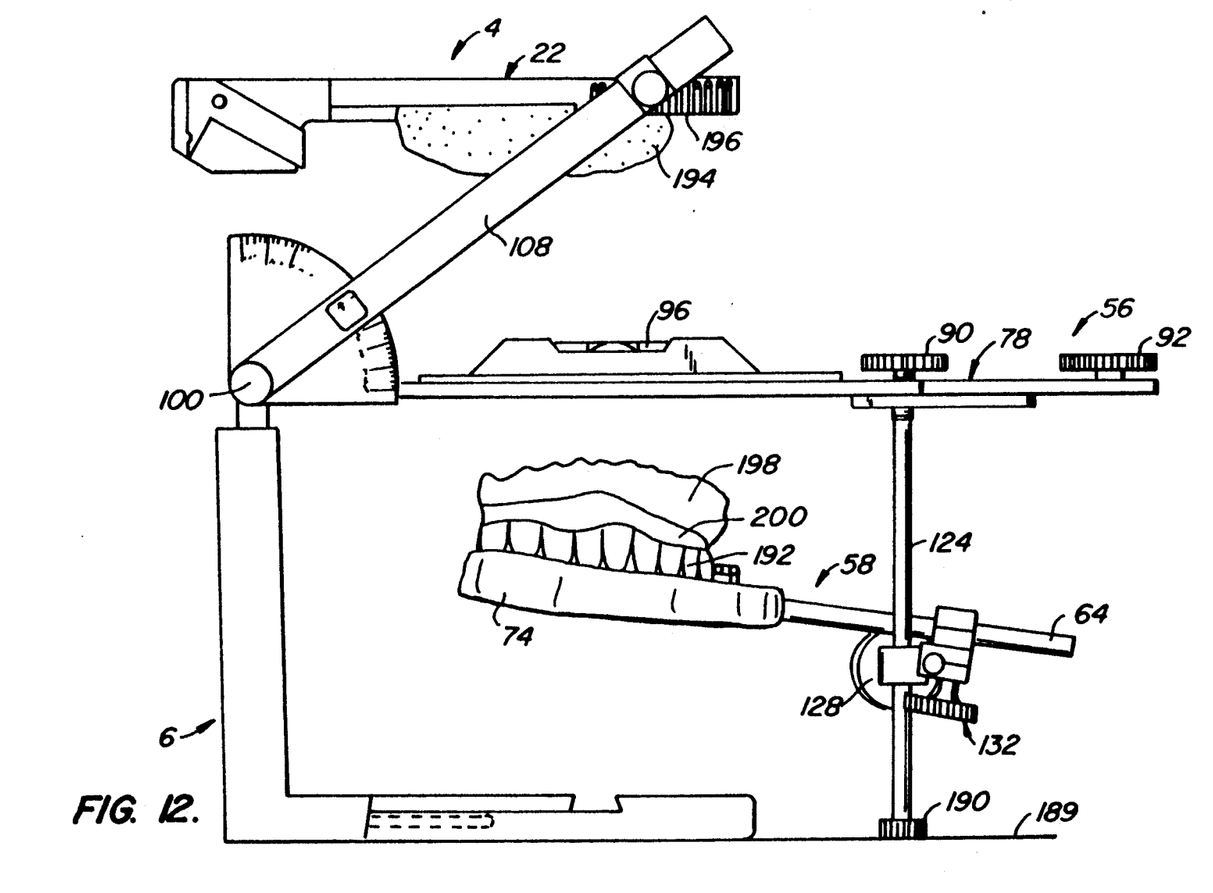
FIG. 12 illustrates the facebow and the bite fork of FIG. 10 mounted to the lower part of the simulator of FIG. 1. The maxillary cast is inserted into the indents of the waxed bite fork and fresh plaster is added to the lower portion of the upper mounting plate and to the upper part of the maxillary cast. The upper part of the simulator carrying the fresh plaster is connected to the lower part at the TMJs. The fresh plaster of both parts meet to allow the maxillary cast to be mounted to the upper part of the simulator.

The facebow 56 and bite fork 58 unit is attached to simulator 2 by first removing earplugs 86, which exposes TMJ axis holes 188 (see FIG. 6). The TMJ axis holes 188 of the facebow are mounted on extensions 12. The height of rod 124 matches the distance extensions 12 (and thus estimated TMJ axis 10) are from the support surface 189 upon which the apparatus is placed. Assuming surface 189 is horizontal, as shown in FIG. 12, level 96 will indicate that frame 78 is horizontal. Maxillary cast 192, previously made from impressions of the patient's teeth, is inserted into the tooth imprints in wax 74 on bite fork 58. Fresh mixed plaster 194 is applied to the inferior portion 196 of superior anterior part 22. Fresh plaster 198 is applied to the exposed, superior portion 200 of maxillary cast 192. Upper part 4 is then positioned onto lower part 6 with surfaces 52, 53, 54 engaging extensions 50. Part 22 is positioned at a horizontal orientation by use of a support 202; see FIG. 13. Support 202 has a laterally extending end 204 which fits within mounting hole 40. This allows fresh plaster 194, 198 to flow together, whereupon the plaster is allowed to set.

Figure 14:
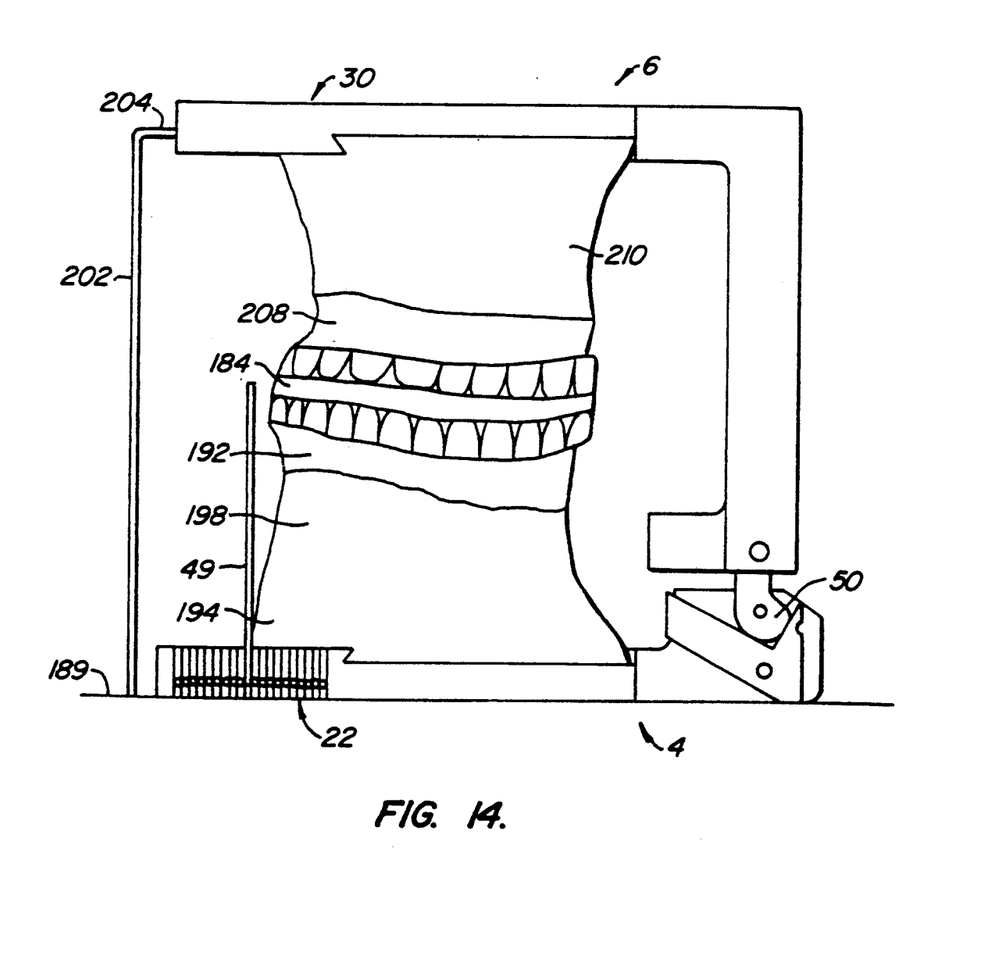
FIG. 14 illustrates the apparatus of FIG. 13 after inversion of the apparatus, with the wax bite shown in FIG. 11 orienting the mandibular cast to the maxillary cast, and after fresh plaster has been positioned between the mandibular cast and the lower mounting plate of the lower part of the simulator, the anterior end of the lower part being supported at a horizontal attitude by a support wire.

After the plaster has set, the facebow 56 and bite fork 58 unit is removed from simulator 2 and the simulator is inverted, as shown in FIG. 14. End 204 of support 202 is removed from hole 40 and then inserted into hole 42 in part 30. Hole 42 is appropriately positioned to cause part 30 to be slightly off from horizontal when simulator 2 is resting on horizontal surface 189. This is done to increase the interarch height between parts 22, 30 a certain distance, such as 2 mm, to accommodate the thickness of the wax wafer 184 which is positioned onto the maxillary cast to provide support for a mandibular cast 208. Fresh plaster 210 is used to mount mandibular cast 208 to anterior part 30. Once plaster 210 has set, simulator 2 can be reinverted without the need to use support 202. An indicator wire or pointer 49, having a tip 216 sized to fit within holes 48, can be slipped into the appropriate groove 44 and hole 48. Holes 46 are in millimeter increments and comply with the facebow scale 98. The linear number learned earlier from where the verticalizer's chain fell relative to the facebow scale is matched to the hole 46 on upper anterior part 22 that is the same linear distance from TMJ axis 104. The A/P treatment goal position for maxillary incisor teeth 72 can thus be displayed directly on simulator 2.

Modification and variation can be made to the disclosed embodiment without departing from the subject of the invention, as defined in the following claims. For example, other methods for supporting upper and lower parts 4, 6, instead of support 202, can be used. Also, a structure which would permit an indicator wire 214 to be continuously positionable along edge 46 could be used in lieu of the discretely positioned grooves 44 and holes 48. Verticalizer 60 and facebow 56 could be made as a one-piece unit; doing so can eliminate the need for special bubble levels because the two normally separate accessories would then be a single unit with their orientations relative to one another fixed.

What is claimed is:

1. A method for determining the anterior/posterior (A/P) goal position for the maxillary central incisor teeth of a patient comprising the following steps:
    locating the existing position of the maxillary central incisor teeth of the patient;
    finding a reference position on the patient's forehead;
    determining any difference in the A/P positions of the existing position and the reference position; and
    using said difference to determine the A/P goal position for the maxillary incisor teeth.

2. The method of claim 1 wherein the determining step includes the step of positioning the patient's head at a generally vertical attitude.

3. The method of claim 2 wherein the determining step includes the step of visually estimating said difference in the A/P positions.

4. The method of claim 1 wherein the finding step is carried out using the center of the patient's forehead as the reference position.

5. The method of claim 4 further comprising the step of measuring the cant of the patient's forehead at the reference position relative to an estimated frontal plane of the patient's head.

6. The method of claim 5 wherein the using step includes the steps of:
    if the cant is equal to or less than about 7°, choosing the A/P goal position as the A/P position of the reference position; and
    if the cant is greater than about 7°, choosing the A/P goal position as the A/P position of the reference position plus about 0.6 mm anterior for each degree of cant greater than 7°.

7. A method for determining the anterior/posterior (A/P) goal position for the maxillary incisor teeth of a patient comprising the following steps:
    freeing the patient's forehead of hair;
    having the patient smile to fully expose the crowns of the maxillary incisor teeth;
    finding a reference position on the patient's forehead;
    imagining a hypothetical line descending from the reference position that parallels the head's estimated midfrontal plane; and
    using said line to determine the A/P goal position for the maxillary incisor teeth.

8. The method of claim 7 further comprising the step of positioning the patient's head at a generally vertical attitude prior to the imagining step.

9. The method of claim 7 further comprising the step of transferring positional information, corresponding to the goal position, to a dental articulator.

10. A method for determining the anterior/posterior, (A/P) goal position for the maxillary incisor teeth of a patient comprising the following steps:
    positioning the patient's head at a generally vertical attitude;
    freeing the patient's forehead of hair;
    having the patient smile to fully expose the crowns of the maxillary incisor teeth;
    finding a reference position on the patient's forehead;
    imagining a hypothetical line descending from the reference position that parallels the head's estimated midfrontal plane;
    measuring the cant of the patient's forehead relative to the hypothetical line;
    if the cant is equal to or less than about 7°, choosing the A/P goal position as the A/P position of the hypothetical line;

if the cant is greater than about 7°, choosing the A/P goal position as the A/P position of the hypothetical line plus about 0.6 mm anterior for each degree of cant greater than 7°; and transferring positional information, corresponding to the A/P goal position, to a dental articulator.

11. The method of claim 10 further comprising the steps of:

inserting a bite fork, including a bite fork extension, into the patient's mouth; and positioning a bite fork extension against the maxillary central incisor teeth.

12. The method of claim 11 further comprising the step of positioning a verticalizer against the reference position on the patient's forehead.

13. The method of claim 12 wherein the verticalizer positioning step includes the steps of:

determining the vertical distance between the midpoint of the most prominent of the maxillary incisor teeth and the midpoint of the center of the forehead, the verticalizer including a protractor element, a tooth element and a coupling element adjustably coupling the protractor element and tooth element;

adjusting the vertical distance between the protractor element and the tooth element;

adjusting the A/P position of the protractor element inversely according to an estimated difference in the A/P positions of the most prominent of the maxillary incisor teeth relative to the reference position;

placing the protractor element against the reference position;

coupling the tooth element to the most prominent of the maxillary incisor teeth; and determining the cant of the forehead at the reference position from the relative angular orientations of the protractor element and the coupling element.

14. The method of claim 13 further comprising the step of leveling the coupling element by moving the patient's head prior to the cant determining step.

15. The method of claim 14 wherein the verticalizer positioning step includes the step of suspending an elongate locating member vertically from a position transversely aligned with the reference position.

16. The method of claim 15 wherein the measuring step includes the step of recording the location of the locating member along a portion of a facebow frame.

17. The method of claim 13 further comprising the steps of physically coupling the tooth element of the verticalizer directly to the bite fork extension.

18. The method of claim 13 further comprising the steps of:

mounting a facebow to the patient's head, the facebow including a frame and ear plugs mounted to the frame, by inserting the ear plugs into the ear holes of the patient; and leveling the frame while the coupling element of the verticalizer is maintained at a horizontal orientation.

19. The method of claim 18 further comprising the step of suspending a locating member vertically from a position associated with the reference position.

20. The method of claim 19 wherein the suspending step is carried out by suspending the locating member vertically from the protractor element of the verticalizer.

21. The method of claim 19 wherein the suspending step is carried out so the locating member passes adjacent a scale portion of the frame of the facebow, said portion including a scale.

22. The method of claim 21 wherein the measuring step includes the step of recording the location of the locating member along the scale portion of the frame.

23. The method of claim 21 wherein the finding step is carried out using the center of the patient's forehead as the reference position.

24. The method of claim 18 further comprising the step of securing the bite fork to the facebow frame to create a fork/frame unit while the frame of the facebow and the leveling element of the verticalizer are horizontal.

25. The method of claim 24 further comprising the step of measuring and recording the angle between the facebow frame and a line coupling the naison on the patient's face and an estimated temporomandibular joint (estimated TMJ) on the facebow, and measuring and recording the distance between the naison and the estimated TMJ.

26. The method of claim 24 further comprising the steps of removing the verticalizer from the fork/frame unit.

27. The method of claim 26 further comprising the step of removing the fork/frame unit from the patient.

28. The method of claim 27 further comprising the steps of:

mounting the fork/frame unit to a first part of a dental articulator, the dental articulator including a second part coupled to the first part at a hinge joint;

leveling the facebow frame;

mounting a first dental cast to the bite fork; and securing the first dental cast to the first part of the dental articulator.

29. The method of claim 28 further comprising the step of physically transferring A/P goal position information to the first part.

30. The method of claim 29 wherein the A/P goal position information is based upon the actual position the reference position and the cant of the patient's forehead at the reference position.

31. The method of claim 29 further comprising the steps of:

inverting the dental articulator;

leveling the second part;

mounting a second dental cast to the bite fork; and securing the second dental cast to the second part.

32. A dental articulator comprising:

an upper part;

a lower part;

A hinge joint, corresponding to the TMJ axis of a patient, pivotally coupling the upper and lower parts; and means for indicating the distance between the anterior/posterior (A/P) position of a chosen point on the patient's forehead and the A/P position of the hinge joint.

33. The articulator of claim 32 wherein the chosen point is the center of the patient's forehead.

34. The articulator of claim 33 wherein the indicating means includes means for indicating an A/P treatment goal position for the patient's maxillary central incisor teeth, the treatment goal position being based at least in part upon the cant of the patient's forehead at the center of the forehead.

35. A dental articulator comprising:

an upper part;
a lower part;
a hinge joint pivotally coupling the upper and lower parts; and
means for indicating the A/P treatment goal position for the maxillary central incisor teeth of a patient, the indicating means including a series of closely-spaced open areas adapted to vertically secure an elongate indicator to the dental articulator at a series of closely-spaced positions.

36. A combination of a dental bite fork and a dental verticalizer comprising:
the dental verticalizer including:
a leveling member including a level; and
a protractor device mounted to the leveling member, the protractor device including a pivotal part positionable against a patient's forehead for indicating the cant of the patient's forehead at a chosen position when the leveling member is horizontal and the patient's head is at a generally vertical attitude;
the dental bite for comprising:
an arch-shaped plate configured for positioning between the maxillary arch and the mandibular arch of a patient;
a handle extending from the arch-shaped plate; and
an extension extending from a chosen one of the arch-shaped plate and handle, the extension having a contact surface positioned to contact an anterior surface of a maxillary central incisor tooth of the patient when the arch-shaped plate is secured between the maxillary and mandibular arches; and
means for coupling the dental verticalizer to the bite fork.

37. A dental facebow, for use in conjunction with a dental articulator, comprising:
a generally U-shaped frame including a base and first and second legs, each said leg having a distal end;
ear plugs at the distal ends;
the frame including an estimated axis for a temporomandibular joint (estimated TMJ axis);
a scale mounted to the frame for measuring the anterior/posterior (A/P) distance from a chosen position on the forehead to the estimated TMJ axis;
a level mounted to the frame for determining when the frame is horizontal.

38. A dental facebow comprising:
a generally U-shaped frame including a base and first and second legs, each said leg having a distal end;
ear plugs at the distal ends;
the frame including an estimated axis for a temporomandibular joint (estimated TMJ axis);
a scale mounted to the frame for measuring anterior/posterior (A/P) distances from the estimated TMJ axis;
a level mounted to the frame for determining when the frame is horizontal; and
a protractor device including an arm pivotally mounted to the frame for pivoted movement about the estimated TMJ axis.

39. The dental facebow of claim 38 wherein the protractor device includes a direct reading angular scale for indicating the angle between the arm and a plane passing through the estimated TMJ axis and lying parallel to the frame.

40. The dental facebow of claim 38 wherein the arm includes a transversely directed rod extending from the arm in a direction generally parallel to the estimated TMJ axis, the rod positionable at positions along the face of the patient.

41. A dental facebow, verticalizer and bite fork assembly comprising:
a dental verticalizer comprising:
a leveling member including a level; and
a protractor device mounted to the leveling member, the protractor device including a pivotal part positionable aganist a patient's forehead for indicating the cant of the patient's forehead at a chosen position when the leveling member is horizontal and the patient's head is at a generally vertical attitude;
a dental bite fork including:
an arch-shaped plate configured for positioning between the maxillary arch and the mandibular arch of a patient;
a handle extending from the arch-shaped plate; and
an extension extending from a chosen one of the arch-shaped plate and handle, the extension having a contact surface positioned to contact an anterior surface of a maxillary central incisor tooth of the patient when the arch-shaped plate is secured between the maxillary and mandibular arches;
means for coupling the verticalizer to the bite fork; and
a dental facebow including:
a generally U-shaped frame including a base and first and second legs, each said leg having a distal end;
ear plugs at the distal ends;
the frame including an estimated axis for a temporomandibular joint (estimated TMJ axis);
a scale mounted to the frame for measuring anterior/posterior (A/P) distances from the estimated TMJ axis;
a level mounted to the frame for determining when the scale is horizontal;
means for coupling the bite fork to the facebow.

42. A dental facebow and bite fork assembly comprising:
a dental bite fork including:
an arch-shaped plate configured for positioning between the maxillary arch and the mandibular arch of a patient;
a handle extending from the arch-shaped plate
an extension extending from a chosen one of the arch-shaped plate and handle, the extension having a contact surface positioned to contact an anterior surface of a maxillary central incisor tooth of the patient when the arch-shaped plate is secured between the maxillary and mandibular arches;
a dental facebow including:
a generally U-shaped frame including a base and first and second legs, each said leg having a distal end;
ear plugs at the distal ends;
the frame including an estimated axis for a temporomandibular joint (estimated TMJ axis);
a scale mounted to the frame for measuring anterior/posterior (A/P) distances from the estimated TMJ axis;
a level mounted to the frame for determining when the scale is horizontal;

means for coupling the bite fork to the facebow; and;

a protractor device including an arm pivotally mounted to the frame for pivoted movement about the estimated TMJ axis.

43. The assembly of claim 42 wherein the protractor device includes a direct reading angular scale for indicating the angle between the arm and a plane passing through the estimated TMJ axis and lying parallel to the scale.

44. The assembly of claim 42 wherein the arm includes a transversely directed rod extending from the arm in a direction generally parallel to the estimated TMJ axis, the rod positionable at positions along the face of the patient.

45. A dental verticalizer comprising:

a superior horizontal member including a level; and a protractor device mounted to the superior horizontal member, the protractor device including a pivotal part positionable against a patient's forehead for indicating the cant of the patient's forehead at a chosen position when the superior horizontal member is level and the patient's head is at a generally vertical attitude.

46. The verticalizer of claim 45 wherein the protractor device includes a direct reading protractor pivotably mounted to the superior horizontal member.

47. The verticalizer of claim 45 further comprising:

an inferior horizontal member positioned beneath the superior horizontal member; and means for positioning the inferior horizontal member adjacent the maxillary central incisor teeth of a patient.

48. The verticalizer of claim 47 wherein the positioning means includes a generally vertical member adjustably secured to the superior and inferior horizontal members by a coupling element.

49. A dental verticalizer comprising:

a leveling member including a level;

a protractor device mounted to the leveling member, the protractor device including a pivotal part positionable against a patient's forehead for indicating the cant of the patient's forehead at a chosen position when the leveling member is horizontal and the patient's head is at a generally vertical attitude; and an elongate, vertically oriented locating member pendulously supported from the protractor device to hang along the side of the patient's face.

50. The verticalizer of claim 49 wherein the locating member hangs nominally from a position transversely aligned with the chosen position on the patient's forehead.

51. The verticalizer of claim 49 further comprising means for adjusting the anterior/posterior (A/P) position of the locating member according to the cant of the patient's forehead.

52. The verticalizer of claim 51 wherein the A/P position adjusting means includes means for making no adjustment of the A/P position for angles of cant less than a chosen amount.

53. The verticalizer of claim 52 wherein the chosen amount is about 7°.

54. The verticalizer of claim 53 wherein the A/P position adjusting means increases the A/P position by about 0.6 mm for each degree of the angle of cant above 7°.

55. A dental verticalizer comprising:

a leveling member including a level;

a protractor device mounted to the leveling member, the protractor device including a pivotal part positionable against a patient's forehead for indicating the cant of the patient's forehead at a chosen position when the leveling member is horizontal and the patient's head is at a generally vertical attitude;

means for positioning the protractor device relative to the maxillary central incisor teeth of a patient, the positioning means including a generally vertical member adjustably secured to the leveling member by a coupling element; and the leveling member including a scale for indicating the position of the coupling element along the leveling member.

* * * * *